United States Patent [19]

Makosza et al.

[11] Patent Number: 4,962,198

[45] Date of Patent: Oct. 9, 1990

[54] PROCESS FOR THE HYDROXYLATION OF ELECTROPHILIC AROMATIC COMPOUNDS

[75] Inventors: Mieczyslaw Makosza; Krzysztof Sienkiewicz, both of Warsaw, Poland

[73] Assignee: Bayer Aktiengesellschaft, Leverkusen, Fed. Rep. of Germany

[21] Appl. No.: 376,496

[22] Filed: Jul. 7, 1989

[30] Foreign Application Priority Data

Jul. 27, 1988 [PL] Poland .................................. 273927

[51] Int. Cl.$^5$ .................. C07D 253/07; C07D 277/68; C07D 213/26; C07D 215/26
[52] U.S. Cl. .................................... 544/182; 548/178; 548/550; 546/103; 546/179; 546/296; 546/297; 549/479; 549/63; 568/705; 568/706; 568/707; 568/709; 568/710; 568/711; 568/712

[58] Field of Search ................ 544/182; 548/178, 550; 546/103, 179, 296, 297; 549/479, 63; 568/705, 706, 707, 709, 710, 711, 712

[56] References Cited

U.S. PATENT DOCUMENTS 3,553,271  1/1971  Crene et al. ......................... 260/613
4,182,918  1/1980  Seifert ................................. 568/771

*Primary Examiner*—John M. Ford
*Attorney, Agent, or Firm*—Sprung, Horn, Kramer & Woods

[57] ABSTRACT

The invention relates to a generally applicable process for the hydroxylation of electrophilic aromatic compounds, according to which the electrophilic aromatic compounds are reacted with organic hydroperoxides in the presence of bases.

11 Claims, No Drawings

PROCESS FOR THE HYDROXYLATION OF ELECTROPHILIC AROMATIC COMPOUNDS

The invention relates to a process for the hydroxylation of electrophilic aromatic compounds.

Hydroxylated electrophilic aromatic compounds, such as nitrophenols, nitronaphthols and heteroaromatic hydroxyl compounds substituted by nitro groups, such as nitro-hydroxypyridines, are important intermediates for the preparation of plant-protecting agents, pharmaceuticals and dyestuffs. Owing to their importance as intermediates the most diverse processes have already been devised for the preparation of these hydroxylated eletrophilic aromatic compounds. Up until now these compounds have essentially been prepared by the exchange of substituents, for example by hydrolysis of the corresponding halogen compounds, by diazotising the corresponding amino compounds and hydrolysing the diazonium salts, by oxidising lithium- or magnesium-organic compounds of the corresponding nitroaromatic compounds or by nitrating the corresponding aromatic hydroxy compounds.

The known processes do however have the disadvantage that they are not generally suitable for the preparation of any desired nitrophenols, etc. but only for the preparation of very specific nitrophenols or nitronaphthols.

A process has now been found which is generally applicable for the hydroxylation of electrophilic aromatic compounds; it has been found that a hydroxyl group can be introduced into electrophilic aromatic compounds in a simple manner and with good yields if the electrophilic aromatic compounds are reacted with organic hydroperoxides in the presence of bases.

The hydroxylation of aromatic compounds with organic hydroperoxides is known (see, for example, U.S. Pat. Nos. 3,377,386, 3,553,271 and 4,182,918, and EP-A No. 299,893). Up until now, however, hydroxylation reactions have only been used for nucleophilic aromatic compounds such as benzene, alkylbenzenes, phenols and phenol ethers, etc. and have been carried out in the presence of (Lewis) acids and/or chelating compounds.

It has surprisingly been found that electrophilic aromatic compounds also become capable of being hydroxylated by organic hydroperoxides if the reaction with the hydroperoxides is carried out in the presence of bases.

The invention therefore relates to a process for the hydroxylation of electrophilic aromatic compounds which is characterised in that the electrophilic aromatic compounds are reacted with organic hydroperoxides in the presence of bases.

The bases used are strong bases such as alkali metal hydroxides, for example potassium hydroxide, or—preferably—alkali metal alcoholates or amides, such as sodium methylate, sodium ethylate, potassium tert.-butylate, sodium amide or lithium diisopropylamide.

The bases are used in a quantity of at least 2 equivalents, and preferably in a quantity of 2 to 7 equivalents per mol of electrophilic aromatic compound to be hydroxylated.

The organic hydroperoxides are used in an at least equimolar quantity, and preferably in a quantity of 1 to 3 mols of hydroperoxide per mol of the electrophilic aromatic compound to be hydroxylated. The hydroperoxides used are the organic hydroperoxides customarily used for the hydroxylation of aromatic compounds; these are alkyl hydroperoxides such as tert.-butyl hydroperoxide, aralkyl hydroperoxides such as α,α-dimethylbenzyl hydroperoxide (cumyl peroxide) and acyl hydroperoxides such as formyl, acetyl, propionyl, butyryl, lauroyl and benzoyl hydroperoxide.

The hydroxylation according to the invention is carried out in organic or inorganic solvents. Possible organic solvents are above all non-polar aprotic solvents such as toluene or—preferably—polar aprotic solvents such as dimethylformamide, dimethyl sulphoxide, tetrahydrofuran or dimethoxyethane. Liquid ammonia may preferably be mentioned as the inorganic solvent.

The hydroxylation according to the invention is carried out at temperatures of −30° to +50° C., preferably at temperatures of −25° to +30° C.

In the context of the process according to the invention those aromatic compounds are generally described as electrophilic aromatic compounds in whose aromatic ring systems one hydrogen atom can be replaced by vicarious nucleophilic substitution. This reaction and the compounds which can be employed therein are described, for example, in Acc. Chem. Res. 1987, 282-289. The electrophilic aromatic compounds can be iso- or heterocyclic mono-, di- or polycyclic compounds.

The following may for example be mentioned as representatives of the electrophilic aromatic compounds which can be hydroxylated according to the invention: Nitrobenzenes of the formula

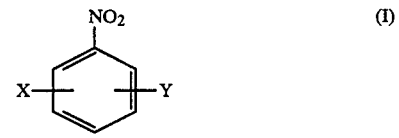

(I)

in which

X and Y, independently of one another, represent hydrogen, halogen, such as fluorine, chlorine, bromine and iodine, optionally substituted $C_1$–$C_4$-alkyl, such as methyl, ethyl, trifluoromethyl and dichlorofluoromethyl; $C_1$–$C_4$-alkoxy, such as methoxy and ethoxy; $C_1$–$C_4$-alkylmercapto, such as methylmercapto and trifluoromethylmercapto; di-$C_1$–$C_4$-alkylamino, such as dimethylamino and diethylamino; cyano; $C_1$–$C_4$-alkylsulphonyl, such as methylsulphonyl; or carboxyl, nitro or hydroxyl, with the proviso that X and Y may not simultaneously be $C_1$–$C_4$-alkoxy and/or di-$C_1$–$C_4$-alkylamino and that, if one of the two substituents X or Y is hydroxyl the other substituent Y or X must be nitro;

1- and 2-nitronapthalenes; aromatic heterocyclic compounds containing a nitro group, such as 2- and 3-nitrothiophenes, 2-nitrofurans, N-alkylated or -arylated 2- and 3-nitropyrroles, 2-, 3- and 4-nitropyridines and 5-, 6- and 8-nitroquinolines; and furthermore electrophilic heteroaromatic compounds without a nitro group, e.g. acridine, benzothiazole and 1,2,4-triazine.

The hydroxylation process according to the invention is generally carried out in such a manner that the solution of the base is added with stirring, at temperatures of −30° to +50° C., to the solution of the electrophilic aromatic compound and the organic hydroperoxide in the selected solvent, the base preferably being dissolved in the same solvent. When the addition of the base has ended the reaction mixture is stirred further at room temperature for a short period, namely for 15 to 120 minutes, depending on the size of the batch. The isolation of the aromatic hydroxy compounds from the reaction mixture is carried out in a known manner by extraction or crystallisation, depending on the physical properties of the aromatic hydroxy compounds produced.

The extraction can, for example, be carried out in such a manner that the reaction mixture is acidified by being stirred into excess aqueous mineral acid, for example 1 to 20% strength aqueous hydrochloric acid. The aqueous-acidic mixture is extracted with a water-immiscible organic solvent, e.g. methylene chloride and the resulting extracts are in turn extracted with aqueous sodium hydroxide solution; after being acidified with mineral acid the combined alkaline extracts are once again extracted with an organic, water-immiscible solvent. After drying the extracts and removing the solvent the aromatic hydroxy compounds are obtained with a high degree of purity.

In the hydroxylation according to the invention the hydroxyl group preferably takes up the ortho- or para-position to the nitro group, in as far as the ortho- or the para-position to the nitro group is unsubstituted. The position of the hydroxyl group entering the aromatic system can be influenced by the reaction conditions, and in particular by the solvent and the base. Thus, for example, hydroxylation of 1-nitronaphthalene in the presence of potassium tert.-butylate in tetrahydrofuran leads predominantly to 1-nitro-2-naphthol, whereas hydroxylation in the presence of sodium methylate in liquid ammonia preferably produces 1-nitro-4-naphthol.

EXAMPLE 1

A solution of 1.40 g (=12.5 mmol) of potassium tert.-butylate in 10 ml of dimethylformamide is added dropwise with stirring at −15° to −25° C. to a solution of 0.79 g (=5 mmol) of m-chloronitrobenzene and 0.70 g (=7.8 mmol) of tert.-butyl hydroperoxide in 5 ml of dimethylformamide. The reaction mixture is finally stirred for 15 minutes at room temperature and is then stirred into 60 ml of 0.5N hydrochloric acid. The aqueous mixture is extracted with methylene chloride and the combined methylene chloride extracts are extracted with 1N aqueous sodium hydroxide solution. The combined alkaline extracts are acidified with hydrochloric acid and then extracted with methylene chloride. After drying the combined methylene chloride extracts over anhydrous magnesium sulphate they are freed from solvent.

0.54 g (=63% of theory) of 2-chloro-4-nitrophenol is obtained in the form of a yellow oil.

2-Chloro-4-nitrophenol is also obtained in a comparable yield when dimethyl sulphoxide is used as the solvent instead of dimethylformamide and the reaction is carried out at +10° C.

EXAMPLE 2

A solution of 1.40 g (=12.5 mmol) of potassium tert.-butylate in 10 ml of dimethylformamide is added to a solution of 0.74 g (=5 mmol) of m-cyanonitrobenzene and 0.70 g (=7.8 mmol) of tert.-butyl hydroperoxide in 5 ml of dimethylformamide, as described in Example 1. The reaction mixture is worked up as described in Example 1.

0.69 g (=84% of theory) of 2-cyano-4-nitrophenol is obtained in the form of yellow crystals; m.p.: 192°-194° C.

EXAMPLE 3

A solution of 1.40 g (12.5 mmol) of potassium tert.-butylate in 10 ml of dimethylformamide is added to a solution of 0.77 g (=5 mmol) of 3-methoxy-5-nitropyridine and 0.70 g (=7.8 mmol) of tert.-butyl hydroperoxide in 5 ml of dimethylformamide under the conditions described in Example 1. The reaction mixture is treated further as described in Example 1.

0.74 g (=79% of theory) of 5-methoxy-3-nitropyrid-2-one (the tautomeric form of 5-methoxy-3-nitro-2-hydroxypyridine) is obtained in the form of yellow crystals; m.p.: 179° C.).

5-methoxy-3-nitro-pyrid-2-one is also obtained in a comparable yield if an equivalent quantity of sodium ethylate is used as the base instead of potassium tert.-butylate.

EXAMPLE 4

A solution of 1.4 g (=12.5 mmol) of potassium tert.-butylate in 10 ml of dimethylformamide is added to a solution of 1.02 g (=5 mmol) of 4-methoxy-1-nitronaphthalene and 0.70 g (=7.8 mmol) of tert.-butyl hydroperoxide in 5 ml of dimethylformamide under the conditions described in Example 1. The reaction mixture is treated further as described in Example 1.

0.78 g (=71% of theory) of 4-methoxy-1-nitro-2-naphthol is obtained in the form of yellow crystals; m.p.: 128°-130° C.

EXAMPLE 5

A solution of 1.40 g (=12.5 mmol) of potassium tert.-butylate in 10 ml of tetrahydrofuran is added to a solution of 0.87 g (=5 mmol) of 1-nitronaphthalene and 0.70 g (=7.8 mmol) of tert.-butyl hydroperoxide in 5 ml of tetrahydrofuran under the conditions described in Example 1. The reaction mixture is treated further as described in Example 1.

0.74 g (=78% of theory) of 1-nitro-2-naphthol is obtained in the form of yellow crystals; m.p.: 101°-102° C.

EXAMPLE 6

A solution of 1.40 g (=12.5 mmol) of potassium tert.-butylate in 10 ml of dimethylformamide is added dropwise with stirring at 0° C. to a solution of 0.87 g (=5 mmol) of 6-nitroquinoline and 0.70 g (=7.8 mmol) of tert.-butyl hydroperoxide in 5 ml of dimethylformamide. The reaction mixture is stirred for 15 minutes at room temperature and is then stirred into 60 ml of 0.5N aqueous hydrochloric acid. The precipitate is filtered off, washed with water and dried.

0.65 g (=68% of theory) of 5-hydroxy-6-nitroquinoline are obtained in the form of yellow crystals; m.p.: 245° C.

EXAMPLE 7

A solution of 8.7 g (=50 mmol) of 1-nitronaphthalene and 8.5 g (=0.56 mmol) of cumyl hydroperoxide in 5 ml of tetrahydrofuran is added dropwise with stirring at a temperature of −30° C. to a solution of 11.1 g (=205 mmol) of sodium methylate in 200 ml of liquid ammonia. After stirring for 30 minutes at −30° C., 10 g of ammonium chloride are introduced in portions and the ammonia is evaporated. The residue is taken up in 200 ml of water and the aqueous solution is acidified with hydrochloric acid and extracted with methylene chloride. The methylene chloride extract is extracted with 1N aqueous sodium hydroxide solution and the alkaline extract is then acidified and once again extracted with methylene chloride.

After drying the solution and concentrating the residue by evaporation in vacuo 8.4 g (=87% of theory) of 4-nitro-1-naphthol are obtained in the form of yellow crystals; m.p.: 166°–169° C.

What is claimed is:

1. A process for the hydroxylation of an electrophilic aromatic compound, which process comprises reacting the electrophilic aromatic compound with an organic hydroperoxide in the presence of a base, wherein the electrophilic aromatic compound is (a) a nitrobenzene for the formula

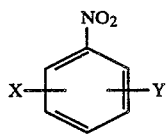

in which X and Y, independently of one another, are hydrogen, halogen, $C_1$–$C_4$-alkyl, $C_1$–$C_4$-alkoxy, $C_1$–$C_4$-alkylmercapto, di-$C_1$–$C_4$-alkylamino, cyano, $C_1$–$C_4$-alkylsulphonyl, carboxyl, nitro or hydroxyl, with the proviso that X and Y may not simultaneously be $C_1$–$C_4$-alkoxy and/or di-$C_1$–$C_4$-alkylamino and that if one of the two substituents X or Y is hydroxyl, the other substituent Y or X must be nitro;

(b) a 1- or 2-nitronaphthalene;

(c) an aromatic heterocyclic compound containing a nitro group, wherein said aromatic heterocyclic compound is 2-nitrothiophene, 3-nitrothiophene, 2-nitrofuran, N-alkylated or -arylated 2- or 3-nitropyrrole, 2-, 3- or 4-nitropyridine or 5-, 6- or 8-nitroquinoline, or (d) acridine, benzothiazole or 1, 2, 4-triazine.

2. The process of claim 1, wherein the hydroxylation is carried out in an organic or inorganic solvent.

3. The process of claim 1, wherein the hydroxylation is carried out in an organic aprotic solvent.

4. The process of claim 1, wherein the hydroxylation is carried out at a temperature within the range of $-30°$ to $+50°$ C.

5. The process of claim 1, wherein the base is used in a quantity of 2 to 7 equivalents per mol of electrophilic aromatic compound to be hydroxylated.

6. The process of claim 1, wherein the base is a strong base selected from the group consisting of an alkali metal hydroxide, an alcoholate and an amide.

7. The process of claim 1, wherein the organic hydroperoxide is used in a quantity of 3 moles of said organic hydroperoxide per mole of the electrophilic aromatic compound to be hydroxylated.

8. The process of claim 1, wherein the organic hydroperoxide is an alkyl hydroperoxide, an aralkyl hydroperoxide or an acyl hydroperoxide.

9. The process of claim 1, wherein the organic hydroperoxide is tert.-butyl hydroperoxide, $\alpha,\alpha$-dimethylbenzyl hydroperoxide, or formyl, acetyl, propionyl, butyryl, lauroyl or benzoyl hydroperoxide.

10. The process according to claim 1, wherein the hydroxylation is carried out at a temperature within the range of $-25°$ to $+30°$ C.

11. The process according to claim 1, wherein X and Y, independently of one another, represent fluorine, chlorine, bromine, iodine, methyl, ethyl, trifluoromethyl, dichlorofluoromethyl, methoxy, ethoxy, methylmercapto, trifluoromethylmercapto, dimethylamino, diethylamino or methylsulphonyl.

* * * * *